(12) United States Patent
Kurtz

(10) Patent No.: US 9,492,184 B2
(45) Date of Patent: Nov. 15, 2016

(54) HIP REPLACEMENT SYSTEMS AND METHODS

(71) Applicant: William B. Kurtz, Nashville, TN (US)

(72) Inventor: William B. Kurtz, Nashville, TN (US)

( * ) Notice: Subject to any disclaimer, the term of this patent is extended or adjusted under 35 U.S.C. 154(b) by 0 days.

(21) Appl. No.: 14/452,468

(22) Filed: Aug. 5, 2014

(65) Prior Publication Data

US 2015/0039095 A1    Feb. 5, 2015

Related U.S. Application Data

(60) Provisional application No. 61/862,109, filed on Aug. 5, 2013.

(51) Int. Cl.
*A61F 2/36*     (2006.01)
*A61B 17/17*    (2006.01)
*A61F 2/30*     (2006.01)

(52) U.S. Cl.
CPC ........... *A61B 17/175* (2013.01); *A61F 2/3609* (2013.01); *A61F 2/30942* (2013.01); *A61F 2002/30616* (2013.01); *A61F 2002/3631* (2013.01)

(58) Field of Classification Search
CPC ........ A61F 2/36; A61F 2/3662; A61F 2002/3631; A61F 2002/3633; A61F 2002/3635; A61F 2002/365; A61F 2002/3652; A61F 2/3609
USPC ................. 623/22.42, 23.21, 23.22
See application file for complete search history.

(56) References Cited

U.S. PATENT DOCUMENTS

| | | | | |
|---|---|---|---|---|
| 4,012,796 A | * | 3/1977 | Weisman | A61F 2/30728 623/23.28 |
| 4,944,762 A | * | 7/1990 | Link | A61B 17/1668 623/23.21 |
| 5,645,600 A | * | 7/1997 | Bimman | A61F 2/30767 623/22.44 |
| 6,494,916 B1 | * | 12/2002 | Babalola | A61F 2/30907 623/23.26 |
| 8,764,844 B2 | * | 7/2014 | McMinn | A61F 2/3601 623/22.44 |
| 2004/0010319 A1 | * | 1/2004 | McTighe | A61F 2/30767 623/23.21 |
| 2004/0024468 A1 | * | 2/2004 | Lualdi | A61F 2/3601 623/22.45 |
| 2004/0138757 A1 | * | 7/2004 | Nadzadi | A61F 2/3609 623/22.11 |
| 2004/0243246 A1 | * | 12/2004 | Lyren | A61F 2/30767 623/22.11 |
| 2005/0027192 A1 | * | 2/2005 | Govari | A61B 5/06 600/424 |
| 2005/0197712 A1 | * | 9/2005 | Bigsby | A61F 2/3601 623/23.27 |
| 2008/0177395 A1 | * | 7/2008 | Stinnette | A61F 2/32 623/20.22 |
| 2008/0200991 A1 | * | 8/2008 | Collins | A61F 2/3603 623/23.12 |
| 2012/0109330 A1 | * | 5/2012 | Forsell | A61F 2/32 623/22.15 |

(Continued)

*Primary Examiner* — Alvin Stewart
(74) *Attorney, Agent, or Firm* — Brainspark Associates, LLC

(57) ABSTRACT

Disclosed are systems, methods, devices and surgical techniques for joint arthroplasty, including implant components that facilitate the position and implantation of a hip replacement using cutting guides and various femoral implant arrangements.

18 Claims, 21 Drawing Sheets

(56) References Cited

U.S. PATENT DOCUMENTS

| | | | | |
|---|---|---|---|---|
| 2012/0116533 A1* | 5/2012 | Forsell | ............ | A61F 2/34 |
| | | | | 623/23.11 |
| 2012/0130503 A1* | 5/2012 | Forsell | ............ | A61F 2/34 |
| | | | | 623/22.15 |
| 2012/0221115 A1* | 8/2012 | Komistek | ............ | A61F 2/32 |
| | | | | 623/22.15 |
| 2013/0211410 A1* | 8/2013 | Landes | ............ | A61B 17/1767 |
| | | | | 606/88 |
| 2014/0276867 A1* | 9/2014 | Kelley | ............ | A61B 17/1746 |
| | | | | 606/89 |
| 2015/0039095 A1* | 2/2015 | Kurtz | ............ | A61B 17/175 |
| | | | | 623/23.21 |
| 2015/0250597 A1* | 9/2015 | Lang | ............ | A61F 2/3609 |
| | | | | 623/22.12 |
| 2015/0335437 A1* | 11/2015 | Bruun Lauritzen | | A61F 2/30756 |
| | | | | 623/23.12 |
| 2016/0045320 A1* | 2/2016 | Klinger | ............ | A61F 2/3609 |
| | | | | 623/23.14 |

\* cited by examiner

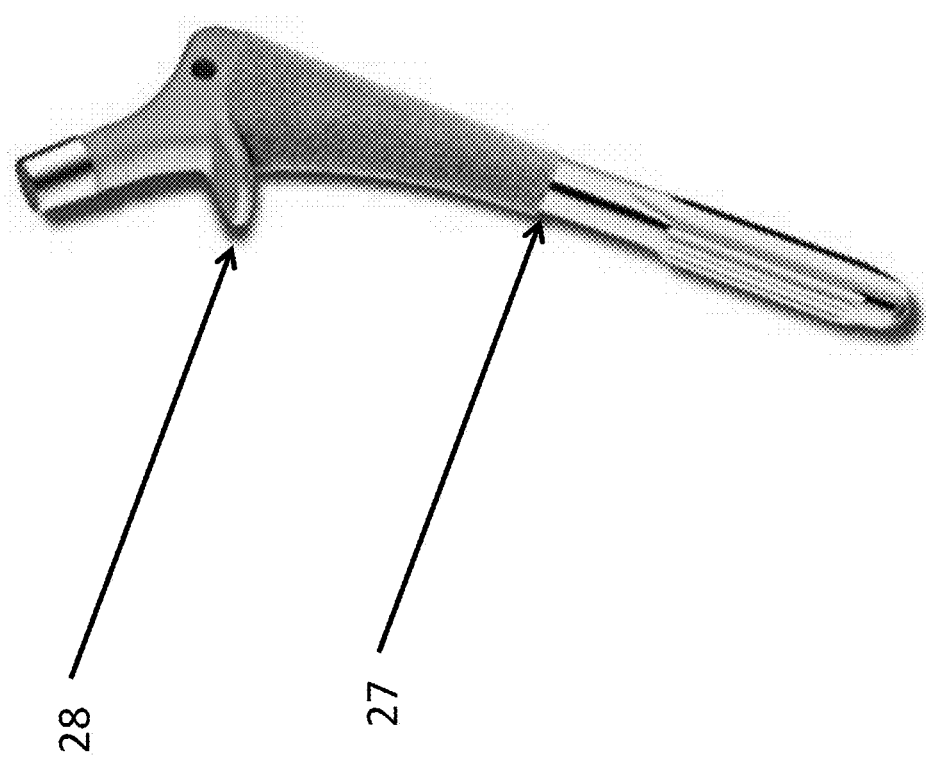

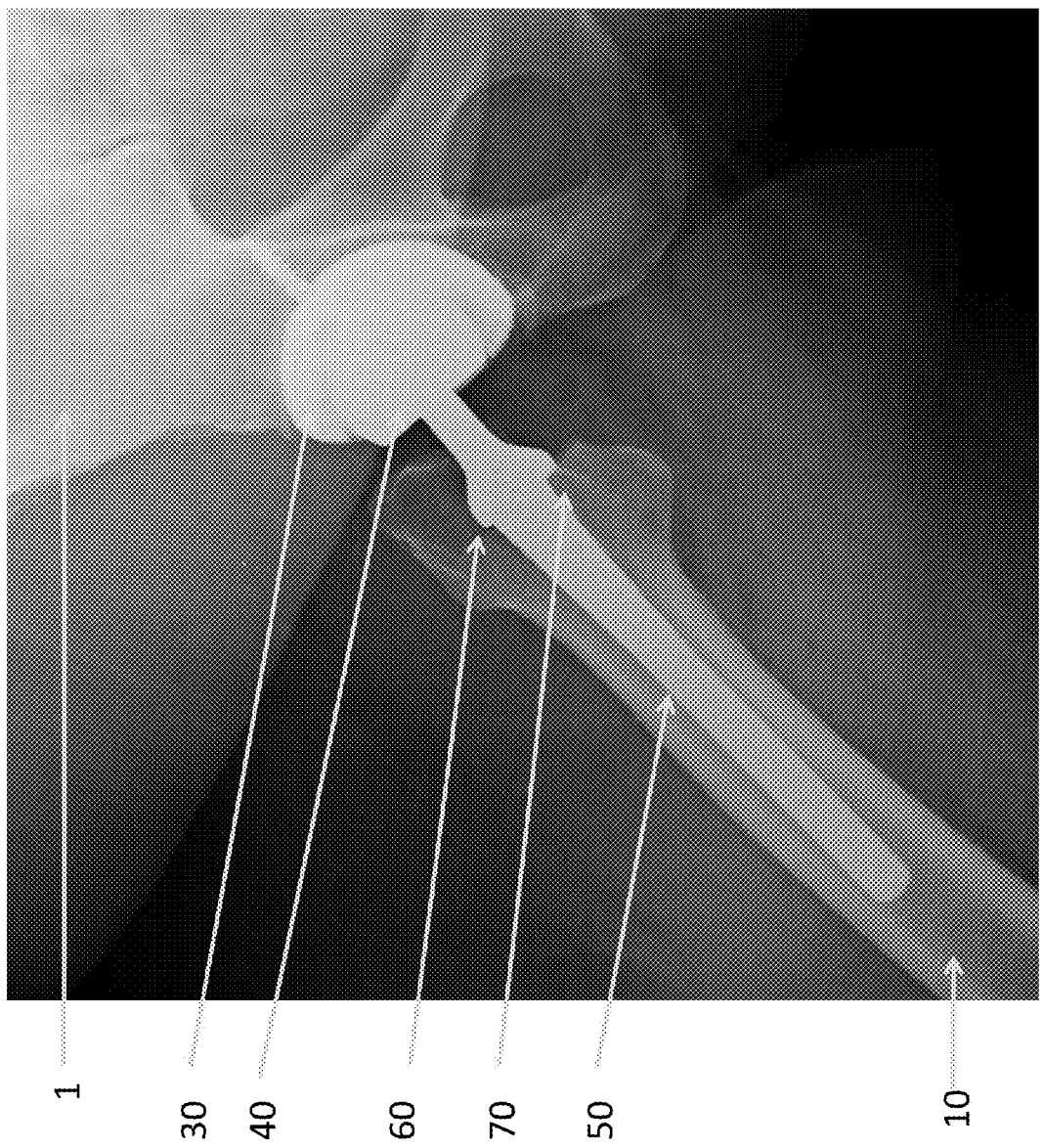

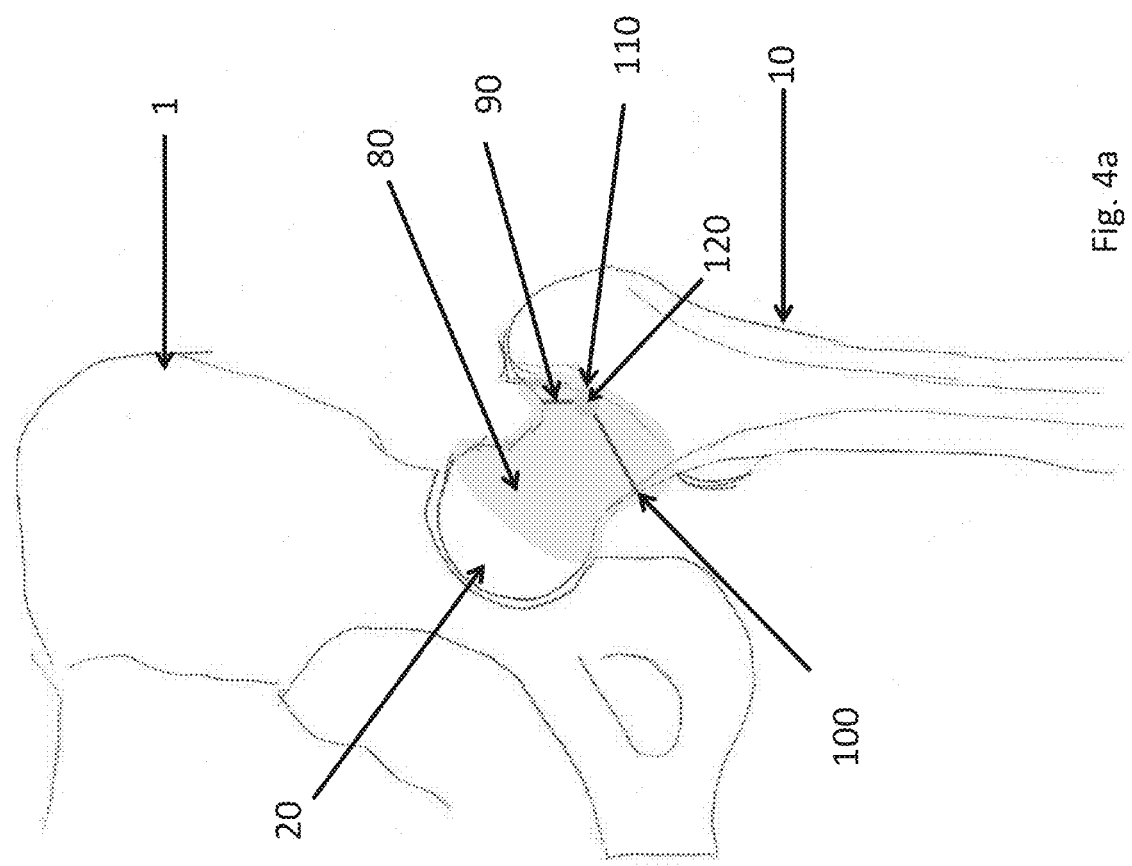

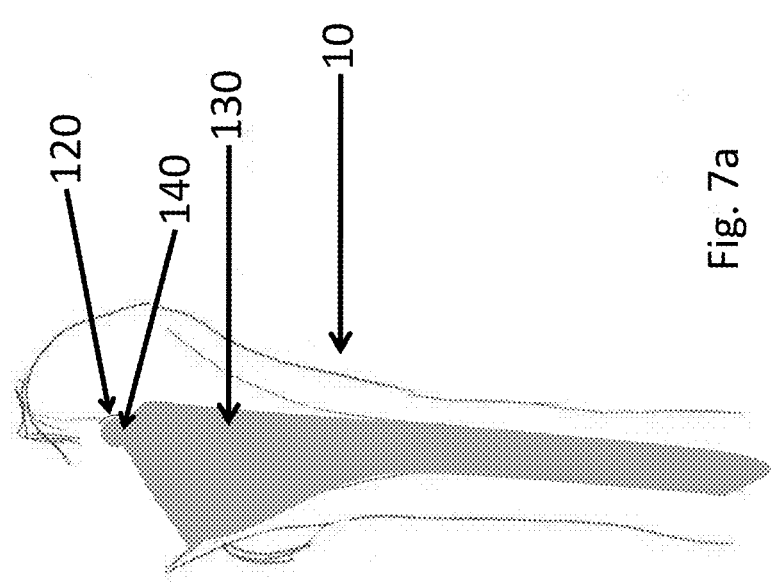

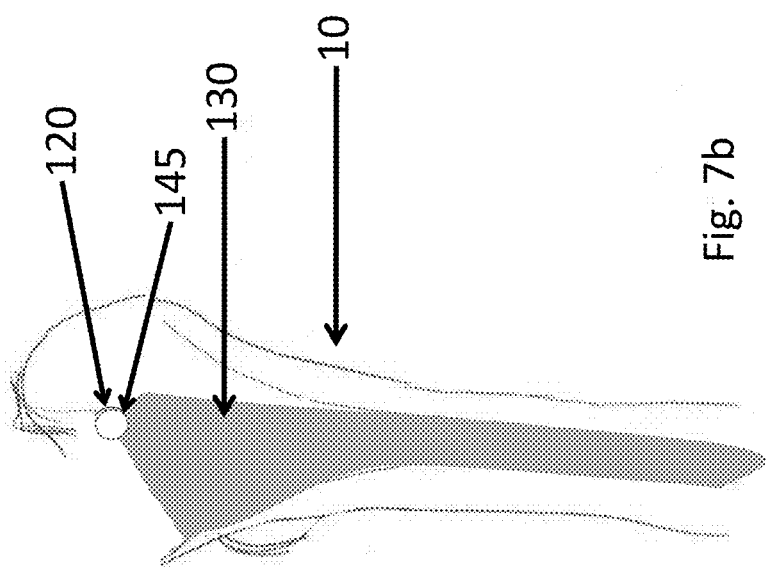

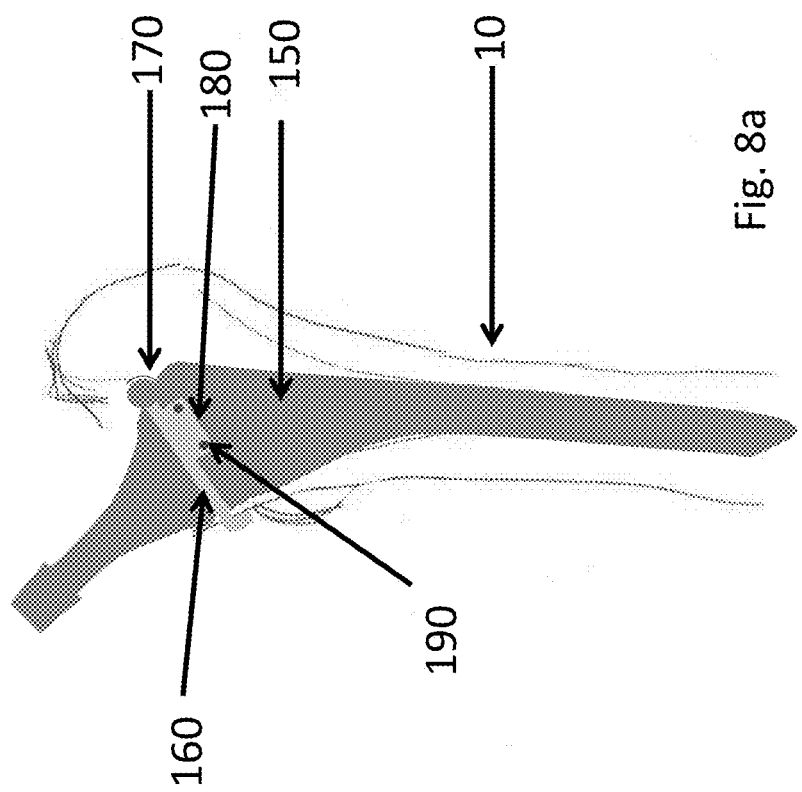

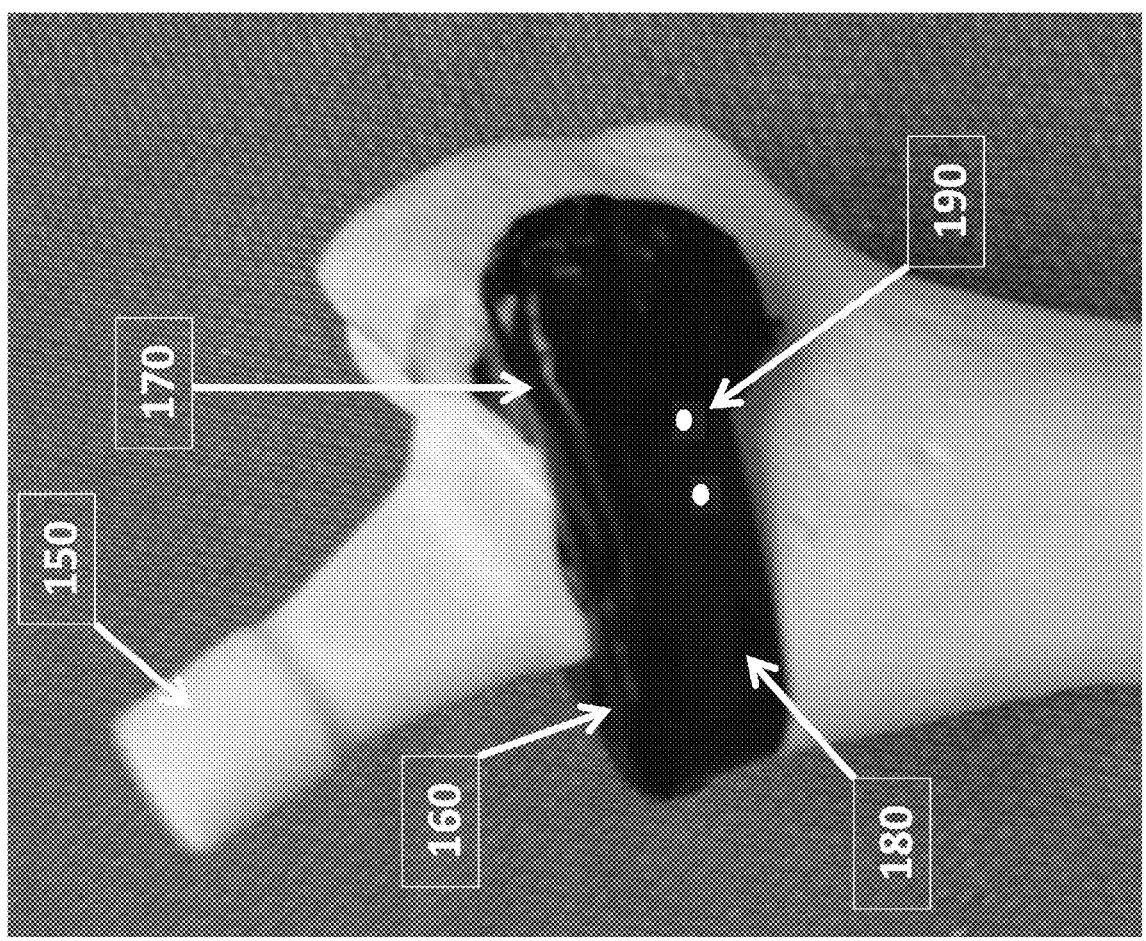

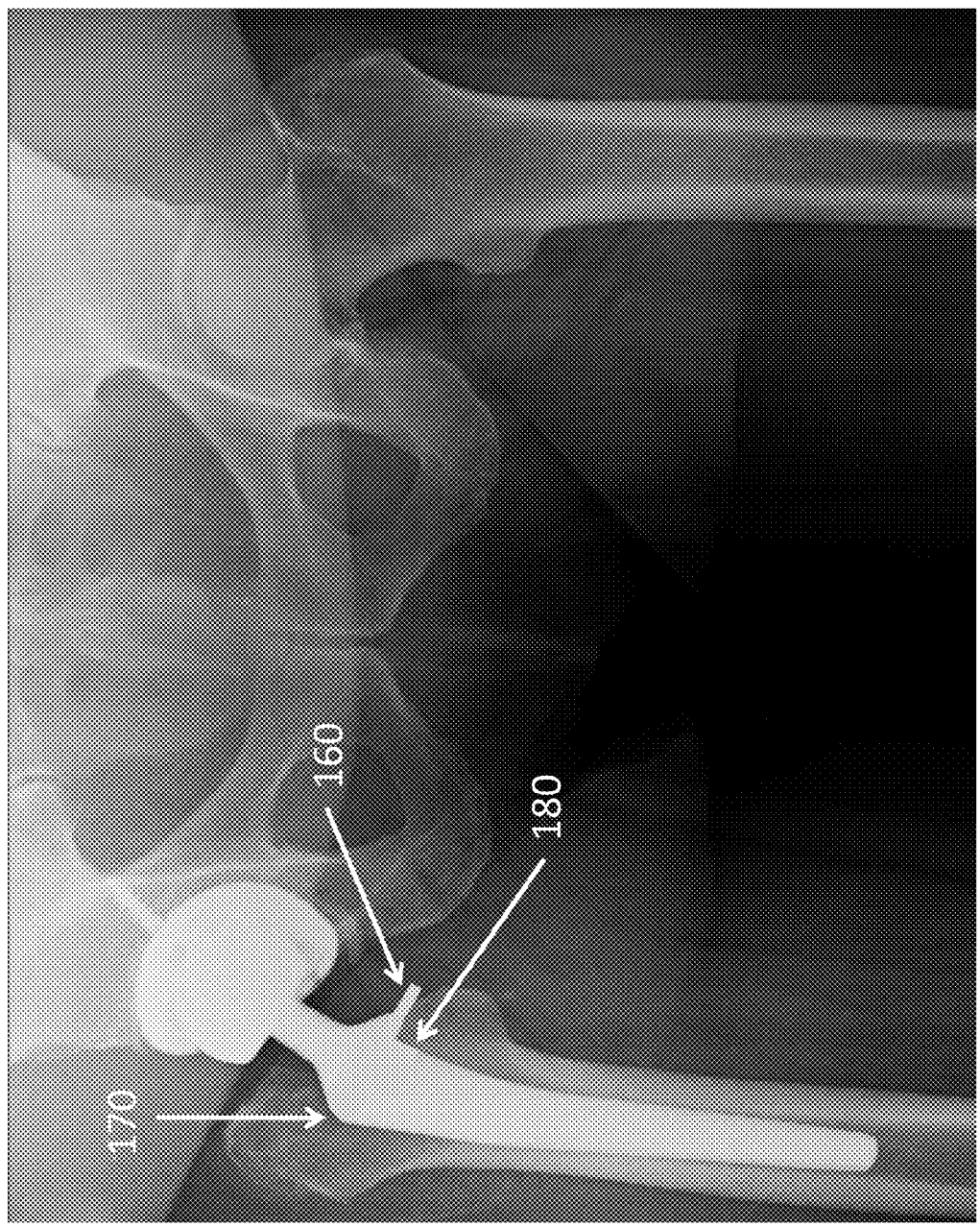

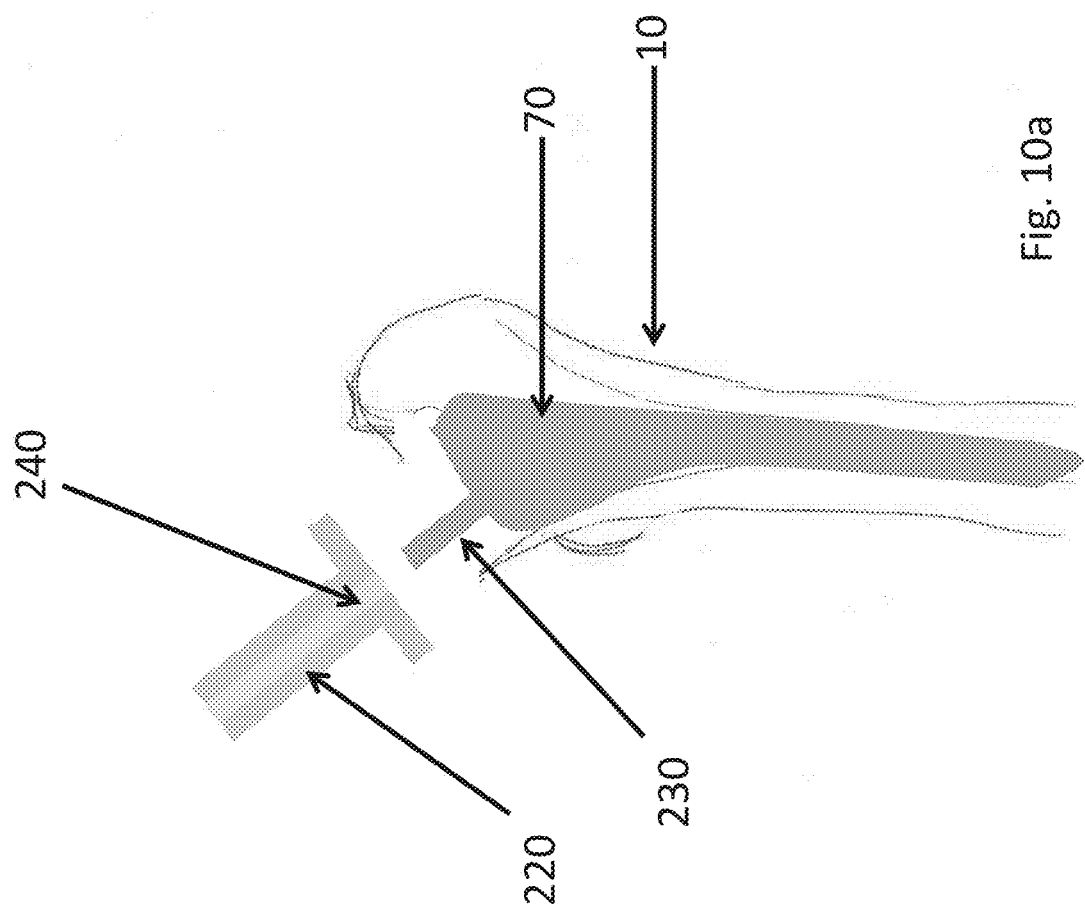

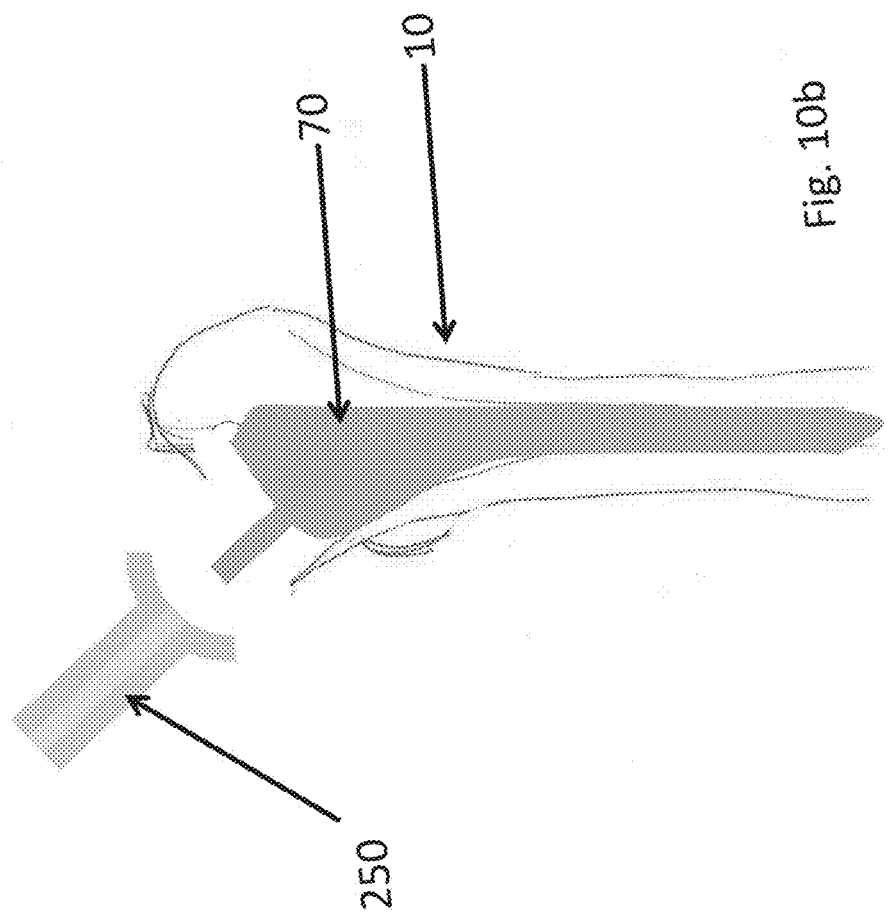

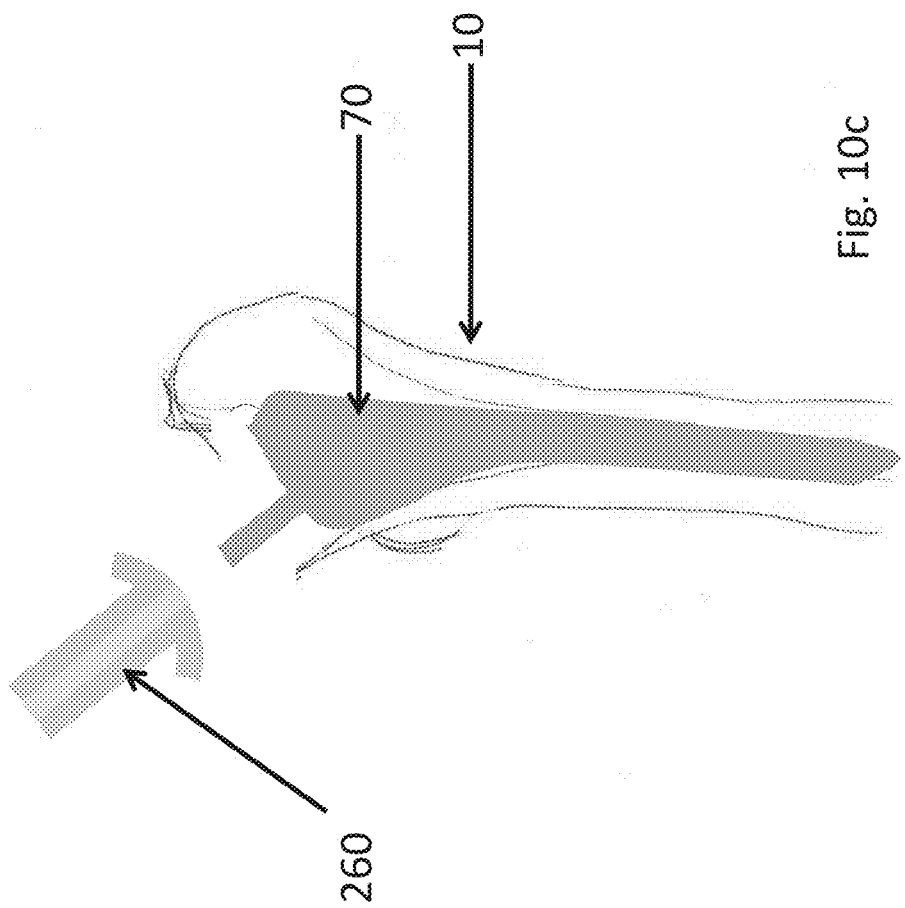

HIP REPLACEMENT SYSTEMS AND METHODS

CROSS-REFERENCE TO RELATED APPLICATIONS

This application claims the benefit of U.S. Provisional Patent Application Ser. No. 61/862,109 entitled "Hip Replacement System with Unique Femoral Prosthesis," filed Aug. 5, 2013, the disclosure of which is hereby incorporated by reference in its entirety.

TECHNICAL FIELD

The invention relates to improved orthopedic implants and surgical implantation procedures, as well as related methods, designs, systems and models. More specifically, disclosed herein are improved methods, designs and/or systems for joint implant components that facilitate the position and implantation of novel designs of hip replacement components, including the use of patient-specific and/or patient-adapted cutting guides.

BACKGROUND OF THE INVENTION

Total hip arthroplasty (also known as a hip replacement) is a commonly performed surgical procedure which involves removing part of a patient's hip joint and replacing the hip joint with metal and/or plastic components. In a typical surgery, the surgeon will often plan the proposed surgical procedure, including estimating the location of the proposed bone cuts (osteotomy) on the templated radiographs before the surgery. The location of the bone cuts on the femoral neck will desirably partially determine the femoral prosthesis location and the patient's ultimate leg length. It is therefore important in an existing hip surgery for the surgeon to make the femoral neck bone cut in the proper location to avoid limb length inequalities.

In general, the femoral bone must be prepared in the appropriate manner with the proper position and angle to accept the intended femoral prosthesis. The femoral prosthesis should also desirably be implanted in the proper position and angle. Errors in either the preparation of the femoral bone or the implantation of the femoral prosthesis can cause leg length discrepancies, offset discrepancies, leg rotational issues, hip pain and/or hip instability issues. Typically, the femoral prosthesis should be positioned down the center of the femoral canal. If the femoral prosthesis is angled within the femoral canal such that the distal tip of the femoral prosthesis is pointing toward the lateral femoral cortex, then the femoral prosthesis is said to be in a varus position. If the femoral prosthesis is pointing toward the medial femoral cortex, then the implant is said to be in a valgus position. Ideally, the distal tip of the femoral prosthesis is pointing down the center of the femoral canal. If a femoral prosthesis is implanted in a varus or valgus position, then the implant may not rest at the appropriate level in the femoral canal, which can alter the leg length and offset. Femoral prosthesis that are implanted in a varus or valgus position may also have a higher failure rate (aseptic loosening, thigh pain, etc.) than a femoral prosthesis that is well sized and well positioned.

The native femoral anteversion is the angle formed between the femoral head and the knee joint as looking down on top of the femoral bone. Desirably, the femoral prosthesis should fit this native femoral anteversion in most situations. Unfortunately, surgeons can accidentally change the rotation of the femoral prosthesis during the preparation of the femoral bone, which can lead to bony impingement, fractures, and/or hip dislocations.

To date, surgical approaches for hip and knee replacements are often fundamentally different in terms of how they are attached to their respective bones. Knee replacements typically are attached to the exterior of the femoral and tibial bone like a cap on the end of the bone. In contrast, hip replacements are typically attached to the inside (i.e., endosteal surface) of the medullary canal. Of course, various exceptions to this general rule exist, such as hip resurfacing (where the femoral component is attached to the exterior of the femoral bone) or knee revision procedures (where a femoral post may be employed). But where the general rule applies, it aptly accounts for why femoral prosthesis can subside into the femoral canal after implantation whereas knee replacement and hip resurfacing prosthesis typically do not subside. Moreover, the fit of the femoral prosthesis inside the femoral canal is not as obvious to the surgeon with hip replacements compared to knee replacements, often because the implant is not visible. In many cases, an undersized or mal-aligned femoral prosthesis in traditional hip replacements can settle further down the femoral canal once the patient starts to walk on the implant.

Many hip replacements have a femoral prosthesis with a collar or ledge that extends outward at the junction of metaphyseal and neck portion of the femoral prosthesis. If properly positioned, this collar could rest against the femoral neck osteotomy so that the femoral prosthesis would resist subsiding down the femoral canal further than was expected. In such a design, the force transmitted across the hip joint could be partially transmitted to the femoral bone through this collar. However, because in this design the femoral prosthesis still loads the femoral bone from inside the bone, the compression of the femoral component into the femoral canal creates hoop stresses that can split or fracture the femoral bone in much the same way as a log splitter can split apart a log.

Performing a joint replacement with patient specific instruments involves obtaining a pre-operative scan of the joint and then manufacturing tools or patient specific guides that precisely fit the bone involved in the joint replacement. The patient specific instruments form a reverse mold of the surface of the bone. When the patient specific guide intimately contacts the femoral bone, the surgeon can be assured the bone cuts are being performed as planned from the pre-operative scan.

BRIEF SUMMARY OF THE INVENTION

The following invention incorporates various surgical techniques, including one or more unique components and techniques for guiding the surgeon into making a femoral neck cut in an appropriate position through a detailed cutting guide. The various features described herein can be utilized to desirably ensure that the surgeon broaches or prepares the femoral canal with the proper anteversion angle as well as the proper varus/valgus angle and proper depth. Various features can be utilized to ensure that the final prosthesis is implanted in the femoral canal in the appropriate anteversion angle, varus/valgus angle, and depth. Lastly, various features and embodiments disclosed and described herein can be utilized to ensure that the torsional and compressive forces on the femoral prosthesis are transferred to the femoral bone in an ideal fashion, including through a unique collar or similar feature on the femoral prosthesis that intimately contacts the endosteal surface, the osteotomy surface, and/or the periosteal surface of the femoral neck at the level of the osteotomy and maximizes contact area between the collar and the bone, thereby desirably minimizing hoop stresses and/or torsion stresses, and alters to a desirable extent some tensile forces to compressive forces.

BRIEF DESCRIPTION OF THE SEVERAL VIEWS OF THE DRAWINGS

The foregoing and other objects, aspects, features, and advantages of embodiments will become more apparent and may be better understood by referring to the following description, taken in conjunction with the accompanying drawings, in which:

FIG. 2 depicts an example of a standard femoral prosthesis with a collar;

FIGS. 3a and 3b depicts an AP and lateral radiograph of a hip replacement;

FIG. 4a depicts a drawing of an AP view of a femoral guide that references the proximal femoral bone;

FIGS. 7a and 7b depicts a femoral broach inserted into the femoral canal to prepare the bone to accept the femoral prosthesis;

FIGS. 8a, 8b and 8c depicts various exemplary embodiments of a femoral prosthesis implanted into the femoral canal;

FIGS. 9a, 9b and 9c depict the AP and lateral radiographs of a variety of collar embodiments attached to an associated femoral prosthesis; and FIGS. 10a, 10b, and 10c depict cross-sectional views of a standard flat calcar reamer, a domed-shaped calcar reamer, and a hemispherical shaped calcar reamer.

DETAILED DESCRIPTION OF THE INVENTION

Figure 1A:
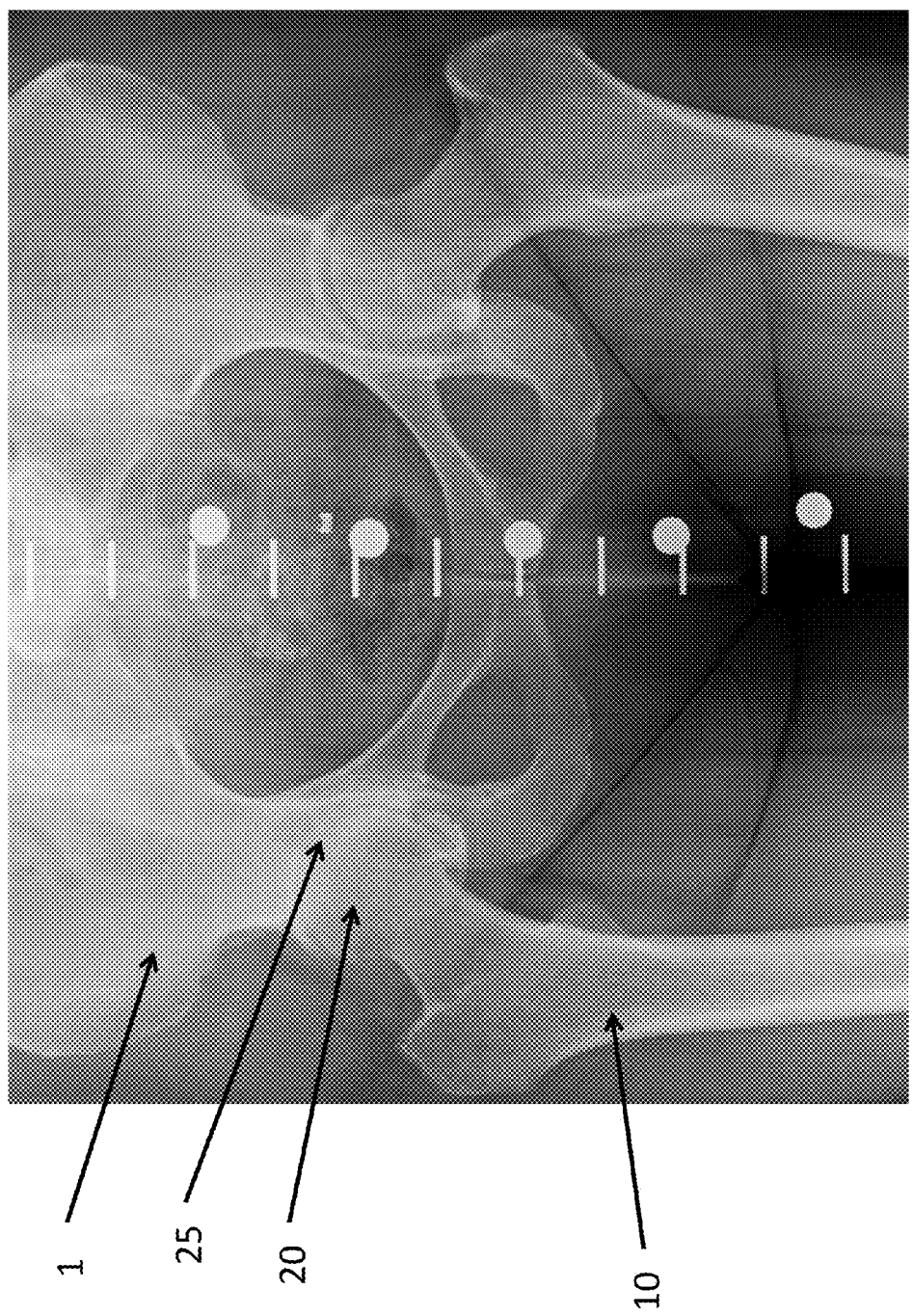
FIG. 1a depicts an anterior/posterior radiograph of an arthritic hip joint and FIG. 1b depicts a lateral radiograph of an arthritic hip joint.
Figure 1B:
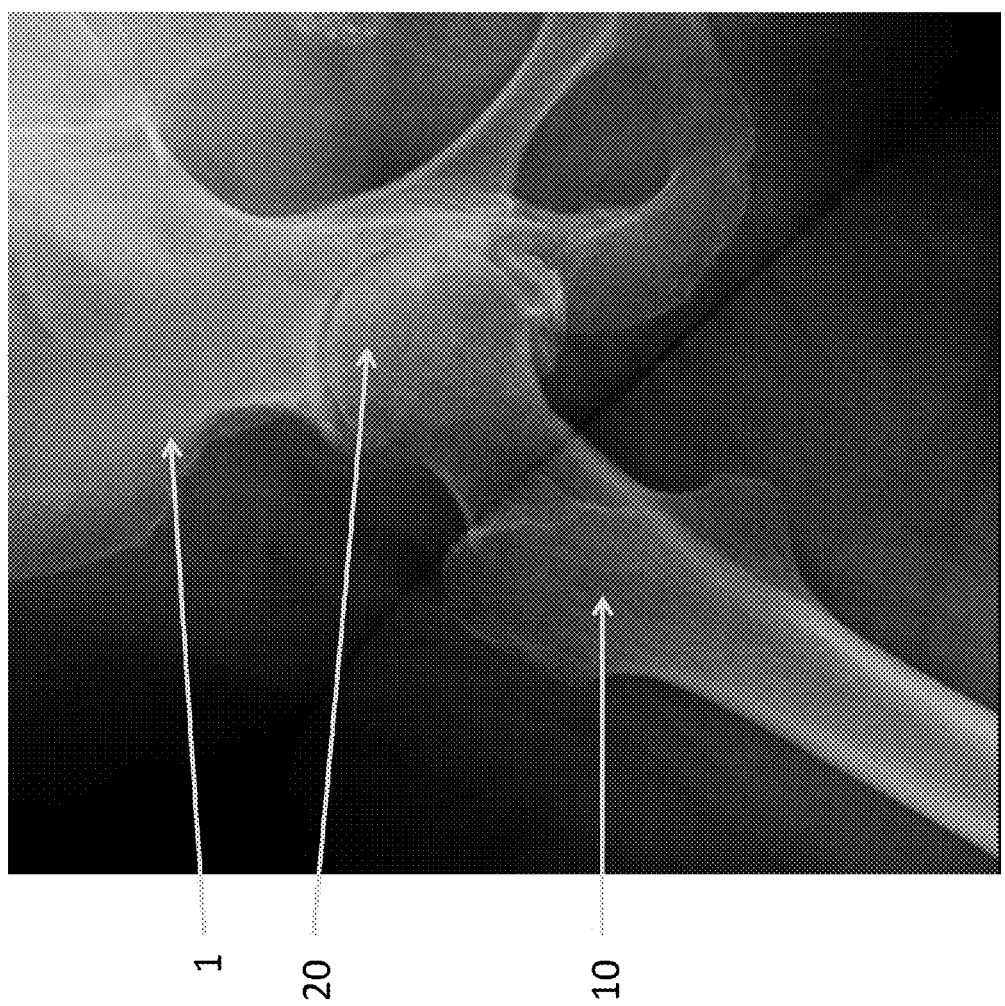

FIG. 1a depicts an anterior/posterior radiograph of an arthritic hip joint and FIG. 1b depicts a lateral x-ray of an arthritic hip joint. The pelvic bone (1) represents the superior portion of the hip joint, the femur (10) represents the inferior portion of the hip joint, and the femoral head (20) rotates in the acetabulum (25).

FIG. 2 depicts an example of a femoral component (27) with a collar (28). The femoral component is also known as a femoral stem or femoral prosthesis. The collar desirably prevents the femoral prosthesis from subsiding down the femoral canal because the collar rests of the calcar osteotomy (femoral neck cut) and prevents further translation of the femoral prosthesis once the collar contacts the femoral osteotomy.

Figure 3A:
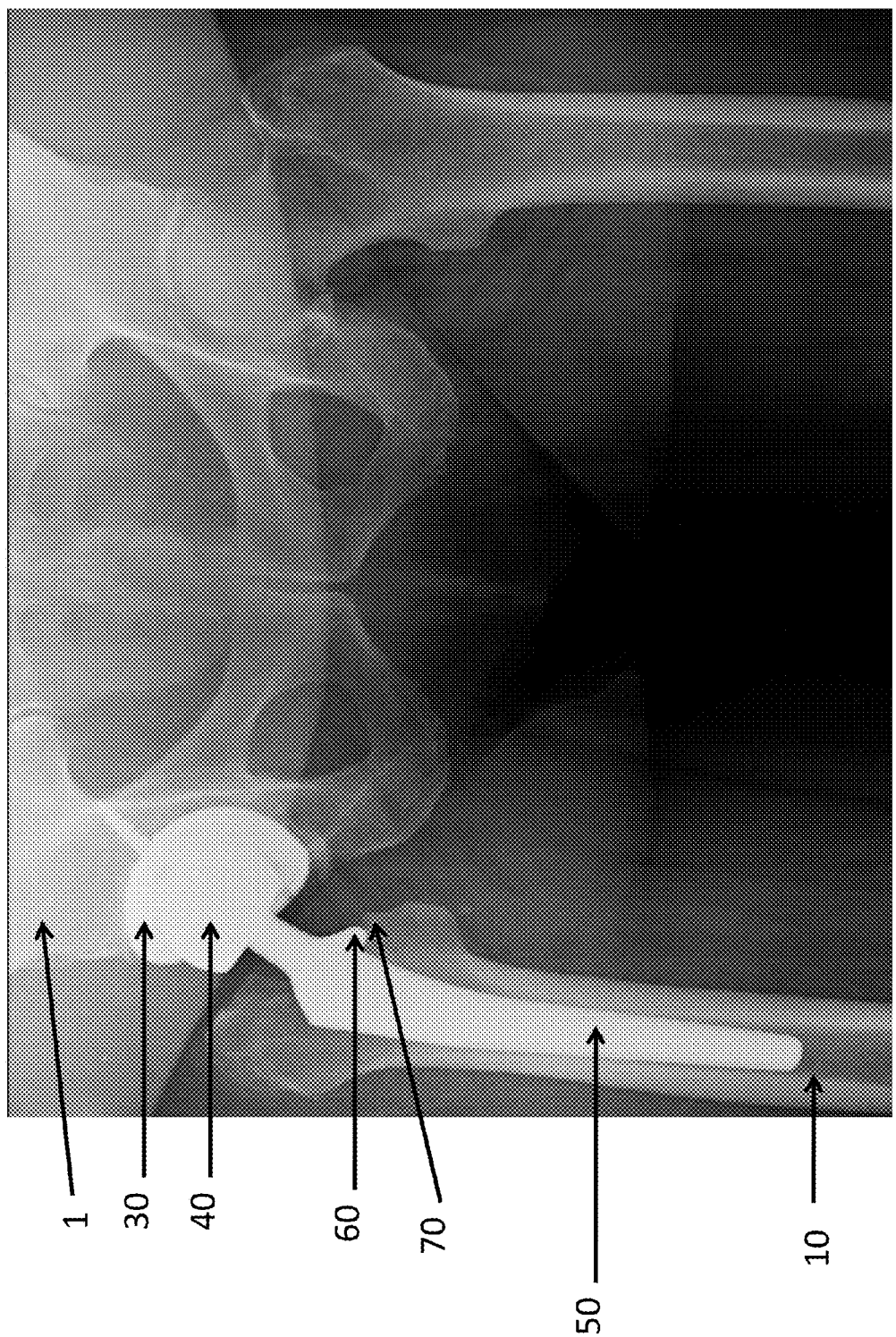

FIGS. 3a and 3b depicts AP and lateral radiographs of a typical hip replacement. The acetabular component (30) has been implanted into the acetabulum. The femoral component or stem (50) has been implanted down the femoral canal to the desired level. The prosthetic femoral head (40) has been attached to the femoral component (50) and articulates with the acetabular component (30). The femoral stem has a collar (60), which rest against the femoral calcar bone (70).

FIG. 4a depicts an AP view of a femoral guide (80) that references a substantial portion of the proximal femoral bone, such as either the anterior or posterior femoral neck. The guide could be patient specific or generic. As part of a pre-operative plan, the surgeon could use non-invasive imaging data or other information to determine his intended surgical approach to the hip joint, and this intended approach would determine whether the femoral guide would reference predominately the anterior femoral neck or posterior femoral neck. In both situations, the femoral guide could reference a significant portion of the superior and inferior femoral neck and femoral head (20) as well.

The femoral guide (80) could contain a drill sleeve (110) that would accept a drill bit (130) that could form an anterior to posterior (AP) hole (120) in the femoral bone at the intersection of the vertical femoral cut guide (90) and the calcar femoral cut guide (100). This AP hole (120) could later be used to ensure the femoral broach and prosthesis were implanted in the proper location. After the surgeon drilled this AP hole (120), they could likely leave the drill bit in the bone and then use the vertical cut guide (90) and the calcar cut guide (100) in the femoral guide to make the appropriate osteotomy in the femoral bone. The drill bit could ensure that the saw blade did not extend beyond the intended osteotomy site, which could help prevent greater trochanter fractures from the saw blade extended beyond the intended osteotomy. Alternatively, the surgeon could drill the AP hole and then remove this femoral guide (80) and insert a different femoral guide (not shown) that had a cylinder that fit inside this AP hole and a saw guide that rested on the surface of the femoral bone to guide a saw blade to make the calcar and vertical cuts. This alternative approach could include features (not shown) to create an improved fixation of the saw guide to the bone to prevent the saw guide from moving while the saw cut the bone. This alternative approach could also drill a second hole in the femoral neck or head for the main purpose of provided the saw guide with additional stability. The femoral head (20) could then be removed from the femur.

The femoral guide could include one or more patient specific soft tissue protectors (such as those disclosed in U.S. Utility patent application Ser. No. 14/059,372, filed on Oct. 21, 2013, and U.S. Provisional Patent Application No. 61/716,571, filed on Oct. 21, 2012, the disclosures of which are incorporated herein by reference in their entireties) along the intended path of the calcar osteotomy and superior femoral neck to desirably prevent the saw blade from inadvertently extended beyond the bone and cutting the hip capsule. The saw blade could be allowed to contact the patient specific soft tissue protector once the saw blade left the femoral bone, instead of the soft tissue surrounding the hip joint.

Figure 5A:
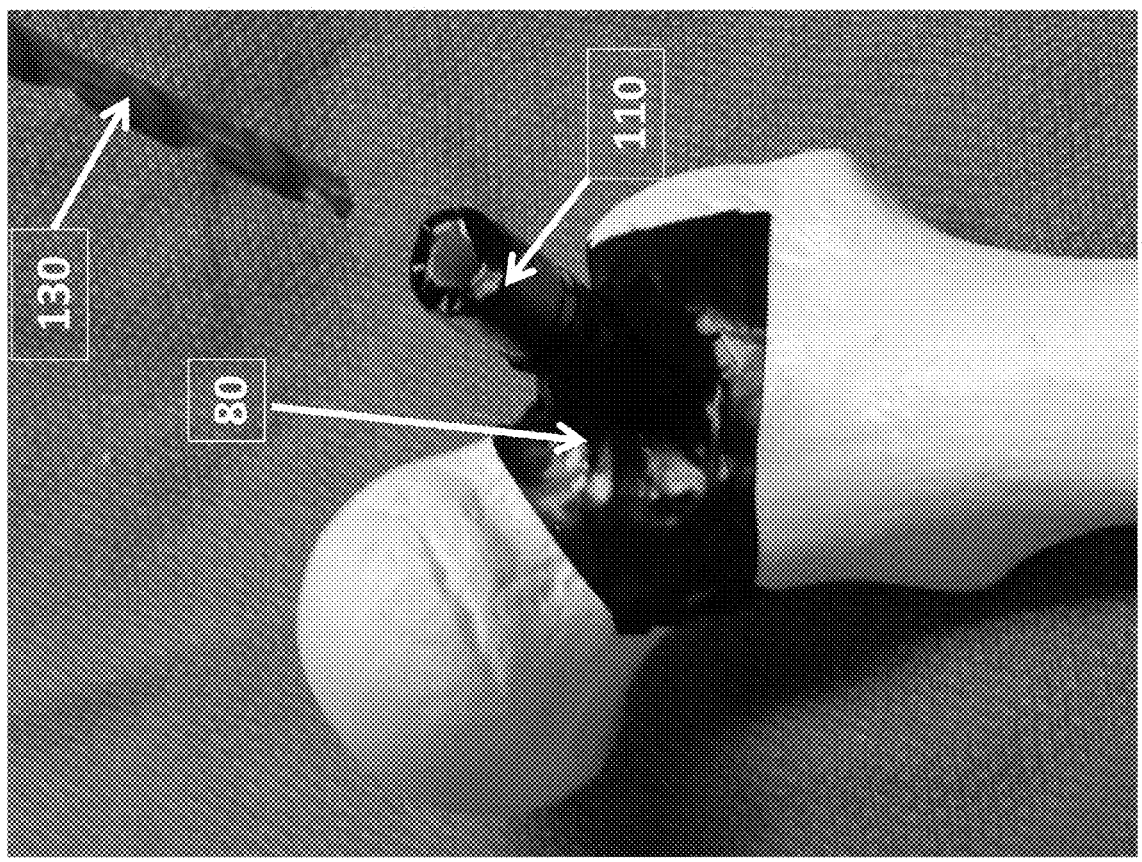
FIGS. 5a and 5b depicts AP views of a femur with and without a femoral guide referencing the anterior femoral neck and other proximal femoral bone.

FIG. 5a depicts a view of a femoral guide (80) superimposed on the radiograph. The femoral guide (80) is shown referencing a large portion of the anterior femoral neck. The AP drill sleeve (110) is shown extending away from and attached to the femoral guide (80). The height of the drill sleeve (110) could be patient specific such that the length of the drill bit (130) minus the height of the drill sleeve (110) would equal the width of the femoral neck. The drill bit (130) would therefore drill through the femoral neck and desirably stop immediately after the drill bit went through the opposite cortex when the head of the drill bit contacted the drill sleeve. The drill bit could be any diameter, but in various embodiments would likely be around 3-5 mm in diameter.

Figure 5B:
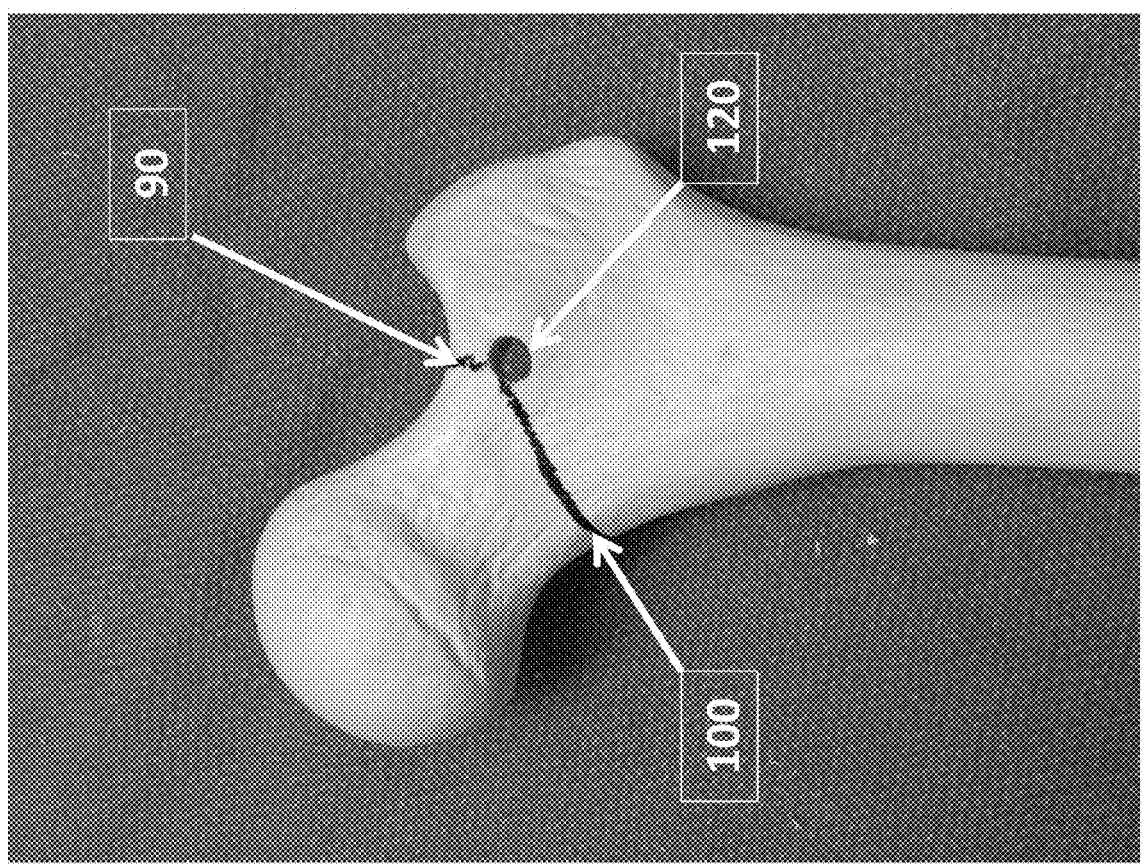

FIG. 5b depicts a view of a proximal femur after the AP hole (120) has been drilled and the femoral guide removed. The purposed vertical femoral osteotomy or cut (90) and the calcar femoral osteotomy or cut (100) are shown with the marked line, but the cuts have not been performed yet.

Figure 6A:
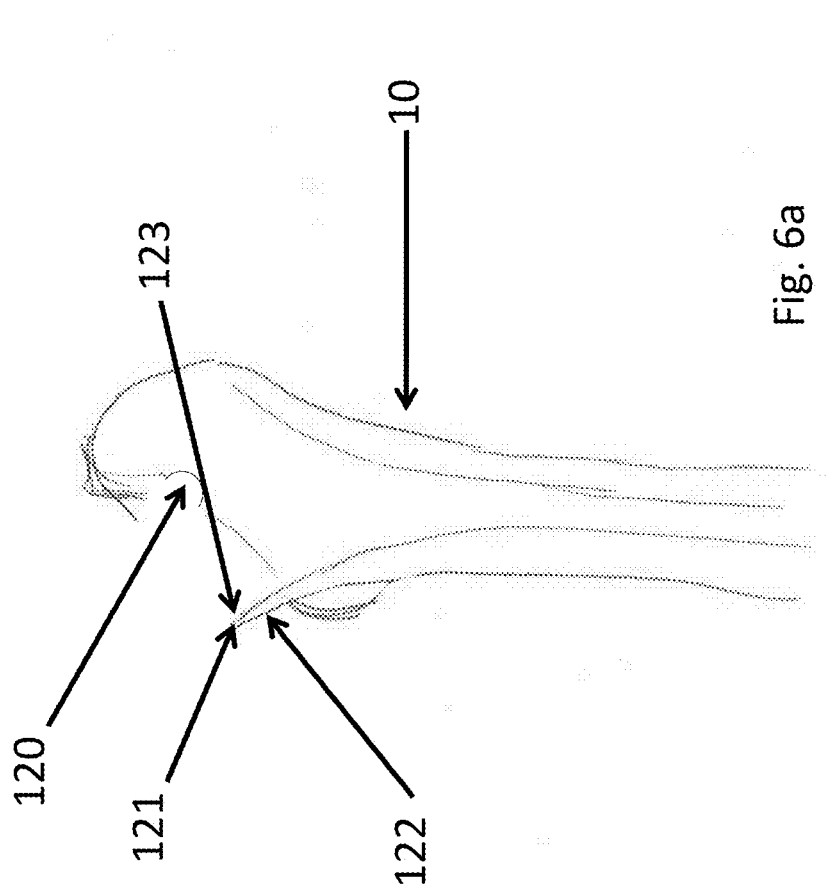
FIGS. 6a and 6b depicts views of the femoral bone after the femoral neck cut (osteotomy) has been performed and the femoral head removed.
Figure 6B:
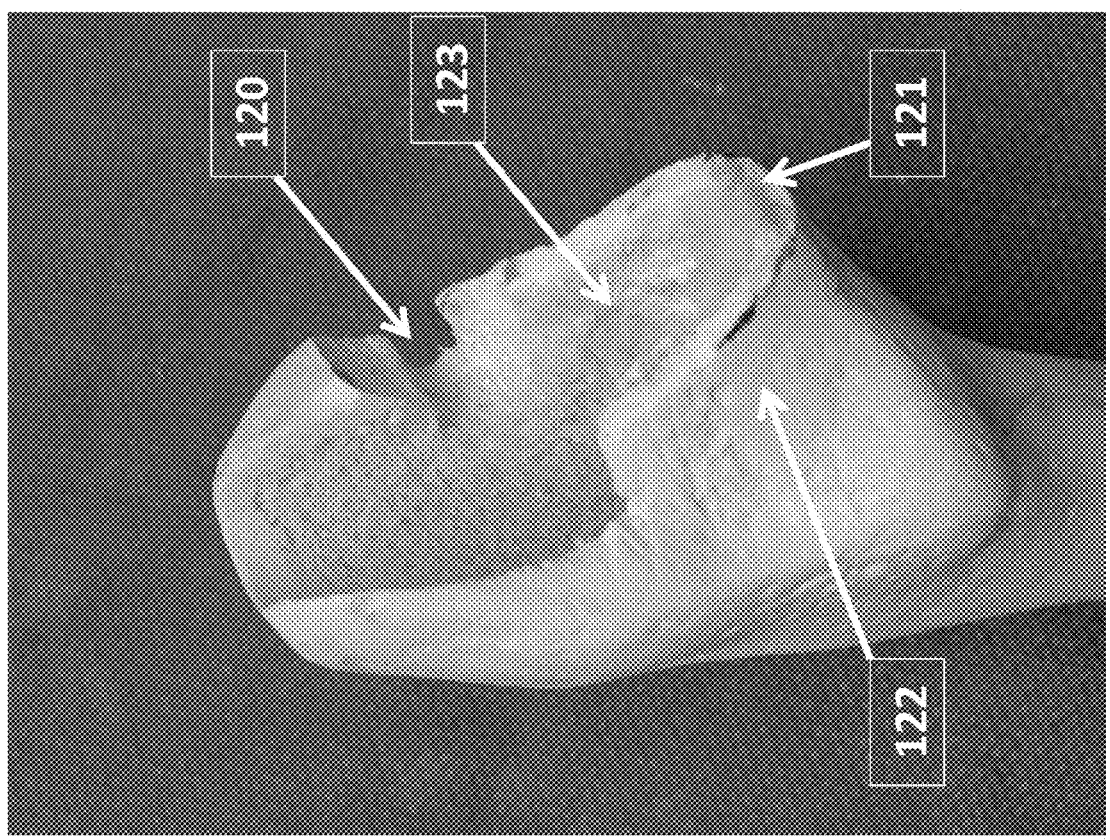

FIGS. 6a and 6b depict the femoral bone (10) after the femoral neck osteotomy has been performed and the femoral head removed. The anterior to posterior (AP) hole (120) is shown at the intersection of the calcar osteotomy (100) and the vertical osteotomy (90) (see FIG. 5b). This AP hole could be located anywhere along the calcar osteotomy and does not necessarily have to be located at the intersection. In this embodiment, this AP hole (120) will be utilized, at least in part, to ensure that the surgeon inserts the broach and femoral prosthesis in the correct anteversion, varus/valgus angle, and depth. Because the femoral head and neck have been removed, the medial and superior portions of the AP hole have been removed and the AP hole can accept an anterior to posterior (AP) bar (140) of the broach or prosthesis as they are inserted down the femoral canal. The femoral neck osteotomy surface (121), and the femoral periosteal surface (122) and the femoral endosteal surface (123) are depicted at the level of the femoral neck osteotomy.

FIG. 7a depicts an exemplary femoral broach (130) inserted into the femur (10) to prepare or machine the bone to accept the femoral prosthesis. If desired, the femoral broach could include an AP bar (140) that extended a few millimeters in the anterior and posterior direction away from the broach much like a collar. This AP bar is shown in a more lateral position than a traditional collar, but could be located anywhere along the osteotomy. This AP bar would desirably be a similar diameter as the AP hole (120) and the drill bit (130). The broach and/or prosthesis would desirably be in the appropriate position when the anterior and posterior portions of the AP bar (140) aligned with the anterior and posterior portions of the AP hole (120). If the surgeon tried to change the femoral anteversion, then the AP bar would desirably no longer key into the AP hole (120). If the surgeon inserted the broach in a varus position, then the AP bar (140) could be medially to the AP hole (120); the surgeon could realize this mistake and remove more bone from the lateral proximal femur to get the broach out of a varus position and into the correct position.

The AP bar (140) on the broach could be removable or elevated on the broach handle so that smaller broaches could be impacted further down the femoral canal to prepare for the next larger broach size. Broaches smaller than the intended prosthetic size can typically extended down into the femoral canal a few millimeters below the osteotomy level. The AP bar (140) could be temporarily removed to allow these small broaches to fully prepare the femoral canal. The AP bar could also be removed so that the surgeon could knowingly change the anteversion of the femoral broach (and calculate the degree of change) if the intra-operative information suggested a change was needed.

FIG. 7b depicts the broach without an AP bar. In this alternative embodiment, the surgeon could also simply rely on a visual marker (145) on the broach, without any type of AP bar, to inform the surgeon about whether the implanted broach position corresponded with the intended broach position. This visual marker shown in FIG. 7b can be a hollow cylinder (145) in the anterior to posterior direction. When the hollow cylinder lined up with the AP hole (120), the surgeon would know the broach was in the correct position regarding the anteversion, varus/valgus, and depth. This hollow cylinder could be limited to just the cross sectional area of the broach so that the hollow cylinder would not interfere with the broach extending below the osteotomy level. The broach could therefore be impacted to its desired level based on the contact between the broach and the medullary canal and endosteal surface. The visual marker (145) would desirably not prevent or interfere with the broach reaching its appropriate and/or desired position. If desired, the hollow cylinder could accept a drill bit so the surgeon could prepare this AP hole for the final prosthesis if there was a difference between the first AP hole preparation and the hollow cylinder of the broach. This preparation might be necessary if the surgeon implanted the broach further down the canal than the pre-operative plan predicted or if the surgeon deliberately or accidentally changed the anteversion or varus/valgus position of the broach relative to the plan.

The femoral broach could include various additional support features, including the use of a collar feature having vertical sides that desirably contact the periosteal bone (122) to ensure that the broach was implanted in the femoral bone in the correct anteversion. The surgeon could also insert a patient specific cap on the femoral neck osteotomy surface (121) that referenced the AP holes (120). This patient specific cap could narrow the width of the proximal femoral canal and help guide the broach into the correct anteversion. The broach could also have vertical markings along the anterior and posterior surface of the broach so the surgeon could align these markings with the AP hole (120) as the broach was inserted into the femoral canal to ensure the implanted femoral anteversion matched the planned femoral anteversion.

FIGS. 8a and 8b depicts an exemplary femoral prosthesis (150) implanted into the femur (10) with an additional collar feature (160 & 180) extending over the femoral neck osteotomy (121) and contacting the periosteal surface (122) of the exterior surface of the femoral neck. The collar feature could be patient specific, modular, or just come in multiple sizes. If the collar feature was patient specific, then the shape and size of the collar could be based off the pre-operative scan and manufactured as a continuous part of the femoral prosthesis to intimately fit the proximal femur. If the collar feature was modular, the surgeon would make a determination during the surgery as to the correct shape and size of the collar based on how the broach fit the bone. The surgeon could then attach a modular collar with the appropriate size to femoral prosthesis before or after it was implanted into the femoral canal. Lastly, the device manufacture could offer the implant with multiple different size collars (i.e. small, medium and large) and allow the surgeon to select the most appropriate sized collar during the surgery.

The collar feature could have a flat horizontal portion (160) that could contact the femoral neck osteotomy (121) and vertical portions (180) that could contact the endosteal (123) and/or periosteal (122) surfaces of the femoral calcar and neck. The collar feature could extend over the neck osteotomy (121) and down the exterior (122) and interior surfaces (123) of the anterior and posterior femoral neck. The flat horizontal portion (160) of the collar feature could intimately contact the neck osteotomy. The axial force from vertical loading of the hip joint could be transmitted across the horizontal portion of the collar to the femoral osteotomy surface (121). The horizontal portion (160) could be the same shape as the cross sectional thickness of the proximal bone at the osteotomy to prevent soft tissue impingement from an oversized collar. The vertical portion (180) of the collar feature could intimately contact the periosteal surface (122) of the anterior and posterior femoral neck and calcar.

The torsion force between the femoral prosthesis and the femoral bone primarily comes from the moment arm of the femoral head being loaded away from the axis of the femoral prosthesis. In various embodiments, this torsion force could be transmitted through the vertical portions of the collar feature to the periosteal and endosteal surfaces of the femoral neck. When torsion stress is applied between the femoral prosthesis and the femoral bone, a traditional prosthesis will typically push on just one side (anterior or posterior) of the endosteal bone. The various embodiments disclosed herein, including the various features described herein, provide an improved prosthesis with collar features that can push on the endosteal surface on one side (i.e. anterior) and the periosteal surface of the other side (i.e. posterior). This improved torsion stability could prevent implant loosening, intra-operative fracture, and postoperative fracture.

Figure 8C:
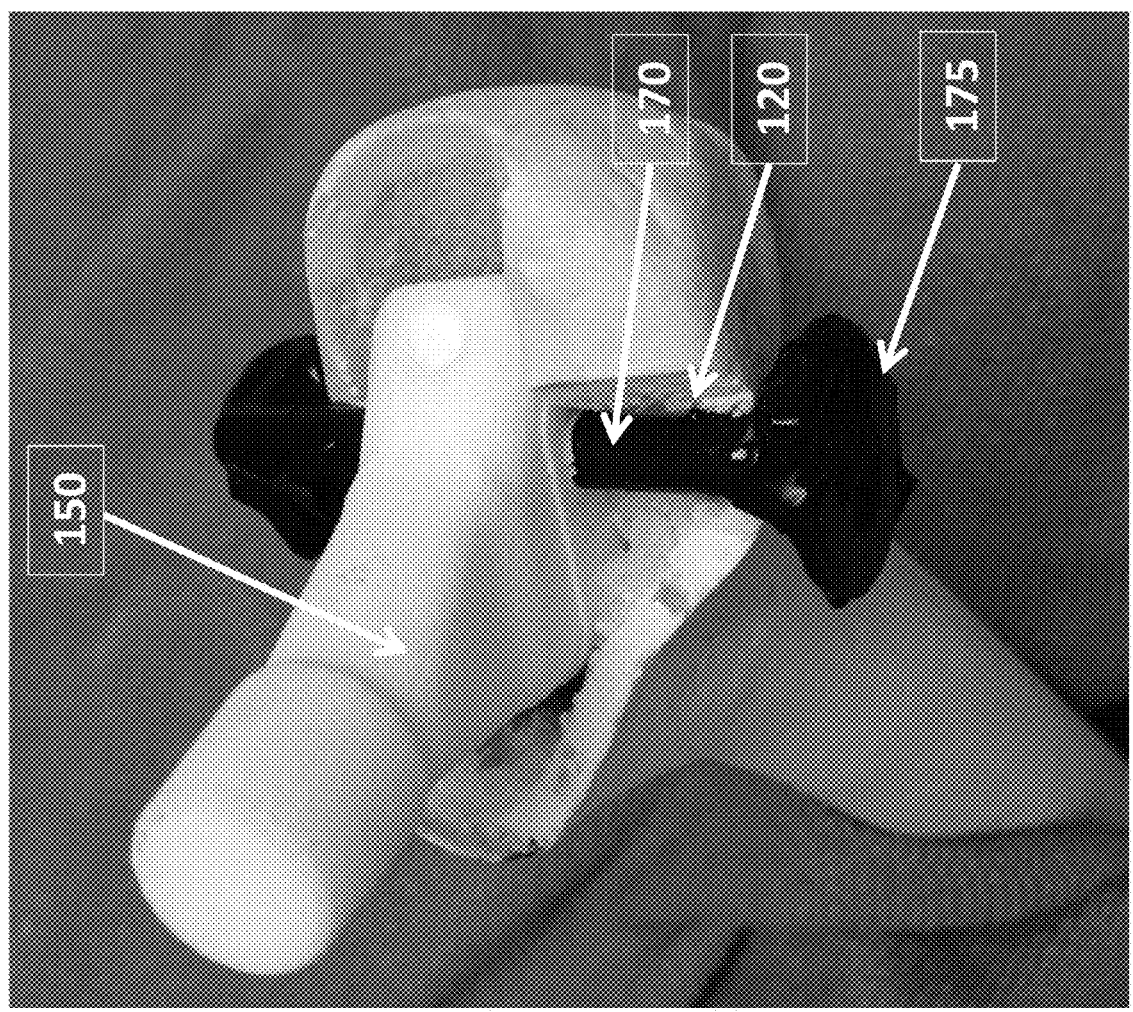

FIG. 8c depicts the AP bar (170) on the femoral prosthesis keying into the AP hole (120) in the femoral bone to ensure that the femoral prosthesis (150) was in the correct anteversion, varus/valgus orientation and depth. The AP bar could be modular such that the femoral prosthesis could have a hole or similar attachment device in the prosthesis. The surgeon could select a length for the anterior and posterior portion of the AP bar based on how far the femoral broach was from the anterior and posterior periosteal surfaces of the proximal femur. The surgeon could then screw the 2 bars into the femoral prosthesis. In various alternative embodiments, the femoral prosthesis could just have a single hole so the 2 bars could be placed through the femoral prosthesis and screw into each other. The cross section of the bar and the hole in the femoral prosthesis could be round to allow for rotation, or could be provided in non-round (i.e., oval, triangular, square or other configurations—with corresponding unique spacing arrangements) to prevent and/or inhibit unwanted rotation.

The femoral prosthesis could include one or more collar features, one or more collar features in combinations with the AP bar (FIGS. 8a and 8b), or just the AP bar (FIG. 8c). The collar feature could be continuous and connected with the AP bar or could comprise a separate tab that was not connected to the AP bar. If the collar feature did not attach to the AP bar, the AP bar (170) could have a vertical wall (175) on each of the anterior and posterior end of the bar that would extend in the inferior direction and contact the periosteal (122) surface of the anterior and posterior femoral neck. The vertical wall of the collar feature could alternatively start at the anterior bar and extend medially around the calcar and then continue around to the posterior bar as shown in FIG. 8b. Both the vertical and horizontal portions of the collar feature could be continuous around the entire femoral neck osteotomy or just small tabs in certain areas to allow better visualization of the contact between the collar and the femoral bone.

Traditional non-collared femoral prosthesis load the endosteal surface of the proximal femoral bone and create hoop stresses in the proximal femur when the femoral prosthesis is driven into the bone during implanting the prosthesis or weight bearing. A femoral prosthesis with a generic "collar" design loads the endosteal surface (123) of the proximal femoral bone and the osteotomy surface (121). The femoral prosthesis described here, in combination with the vertical portion of the collar feature, desirably allows the prosthesis to load the periosteal surface of the proximal femur as well as the endosteal surface and the osteotomy surface. Loading the periosteal surface can help counteract and/or negate the hoop stresses that are generated from loading the endosteal bone. This periosteal loading would desirably generate compressive forces in the proximal femur instead of tensile forces (hoop stresses). The material properties of bone are much stronger in compression than tension, so loading the periosteal surface could decrease femoral calcar fractures.

FIG. 8a also depicts two suture holes (190) in the anterior and posterior portion of the collar. These suture holes could vary in number and be used to reattach the posterior or anterior hip capsule back to the femoral bone. These suture holes could also be used to reattach the greater trochanter if a trochanter fracture occurred during the surgery.

Figure 9B:
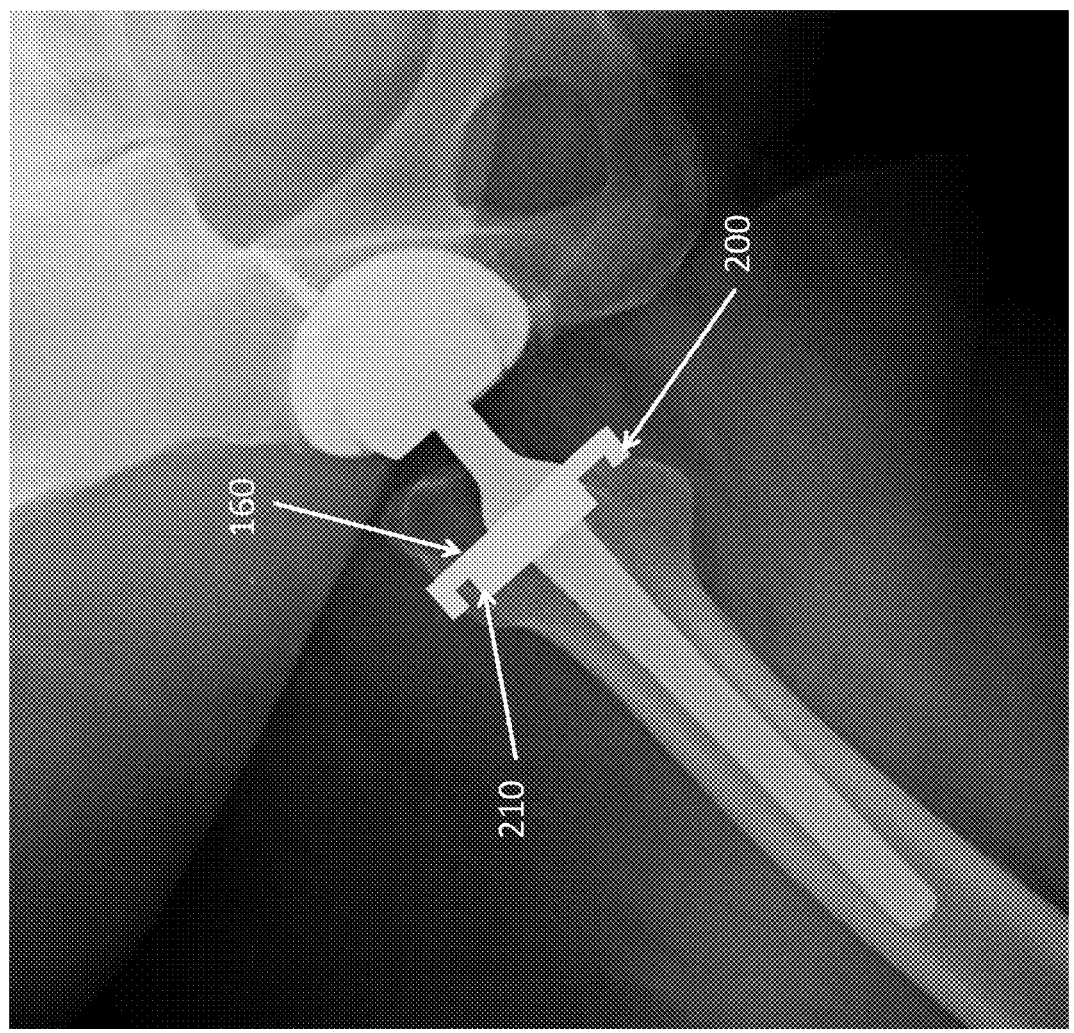
Figure 9C:
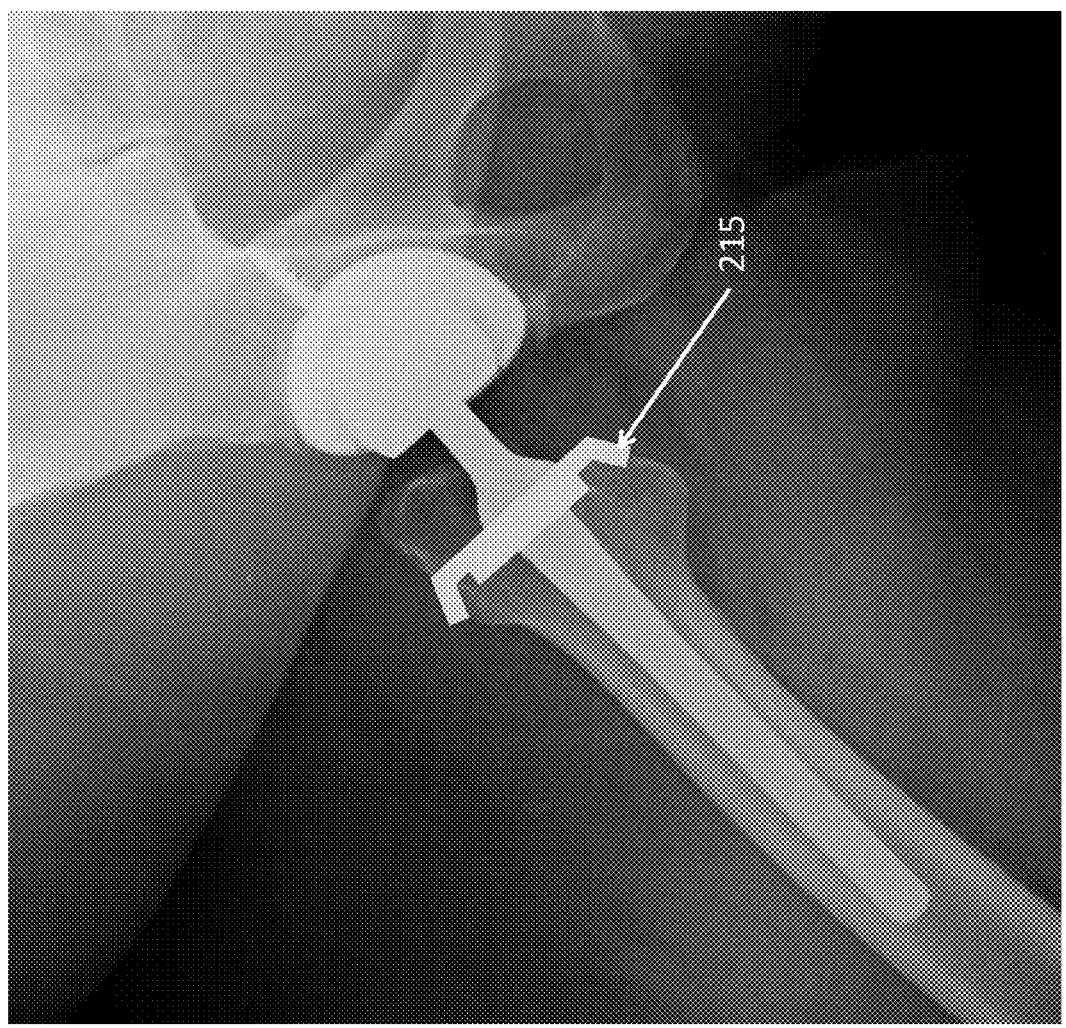

FIGS. 9a, 9b, and 9c depict AP and lateral views of another exemplary collar feature on an exemplary femoral prosthesis. The horizontal portion (160) and vertical portion (180) of the collar feature are shown. The AP bar (170) is shown. FIG. 9b depicts the exterior vertical collar (200) that can be positioned to contact the periosteal surface (122) of the proximal femur and the interior vertical collar (210) that desirably contacts the endosteal surface (123) of the proximal femur. The vertical wall in FIG. 9b is desirably parallel with the axis of the prosthesis. FIG. 9c depicts an exterior vertical collar (215) that is divergent to the axis of the prosthesis, which desirably allows for easier insertion of the prosthesis over the femoral neck osteotomy. This divergent wall could also load the periosteum of the proximal femur and neglect the hoop stresses that are typically generated from the normal prosthesis loading of the endosteal surface of the proximal femur. This arrangement also reduces and/or negates the need for a cerclage wire or other reinforcing arrangement on the proximal femur, as surgeons will occasionally place a cerclage wire around the proximal femur to counteract the hoop stresses on the bone associated with implanting the prosthesis in much the same way as this divergent wall could.

It should be understood that the collar features could be formed in a wide variety of shapes and/or configurations, including shapes and/or features that match and/or substantially conform, to varying degrees, to the underlying anatomy that they contact. For example, the collar features could comprise a hemispherical dome, an oval-shaped dome, a triangular box, a square or virtually any other shape that accomplished some or all of the features of the present invention. In various embodiments, the bone-contacting surface(s) of the collar feature may be non-round and/or irregularly curved and/or otherwise shaped, so as to desirably reduce, prevent and/or inhibit rotation of the implant and/or preferentially load the periosteal bone to varying degrees (instead of the endosteal side of the bone). It should also be understood that, where the collar feature and prosthesis are modular and/or separately formed, the collar feature could include a circular, non-circular and/or irregularly shaped opening formed therein to accommodate the femoral prosthesis.

FIGS. 10a, 10b, and 10c depict cross-sectional views of a standard flat calcar reamer (220), of a reverse domed-shaped calcar reamer (250), and of a hemispherical or domed shaped calcar reamer (260). Flat calcar reamers are well known in the art. The male portion (230) of the femoral broach (70) slides into the female portion (240) of the flat calcar reamer. The flat calcar reamer can rotate around the male portion and remove the necessary femoral bone to make a flat osteotomy surface (121) that maximizes contact between a flat collar and the femoral bone.

FIG. 10b depicts a cross-sectional view of a reverse domed-shaped reamer that could rotate around the male portion of the broach and desirably remove an amount of femoral bone to create a dome shaped osteotomy surface to maximize contact between a reverse dome shaped collar and the femoral bone. If desired, the curvature of the reamer (i.e., modifying the proximal femur) could be slightly flatter than the curvature of the associated collar feature, which could facilitate the collar contacting the outside edge (i.e., periosteal edge) of the bone and loading the bone from the "outside-in." FIG. 10c depicts a cross-sectional view of a hemisphere shaped reamer (260) that could rotate around the male portion of the broach and remove the necessary femoral bone to create a reverse dome (i.e., a hemispherical dome) shaped osteotomy surface that maximizes contact between a hemispherical shaped collar and the femoral bone. The advantage of a dome shaped or reverse dome shaped osteotomy surface can be that axial compression of the implant and bone will desirably increase the contact between the collar and the bone. The torsion stability of the implant could also be improved by this arrangement. The anterior to posterior and medial to lateral stability of the implant could also be improved. The reverse dome shaped osteotomy in FIG. 10b with the dome shaped collar could also help minimize hoop stress from the femoral component loading the femoral canal. The dome shaped collar could help transform the tensile forces (i.e., hoop stresses) into compressive forces, and thereby help prevent calcar fractures that can be seen with implanting a standard femoral prosthesis or loading the femoral prosthesis during weight bearing movement. The vertical portion of the patient specific collar could also help minimize hoop stresses in a manner similar to the cerclage wire does when it is wrapped around the proximal femoral bone, but without the need for such an additional adjunct to the surgery.

If desired, the transitional spacing between the horizontal and vertical exterior surfaces of the collar could be rounded to prevent soft tissue impingement.

The drawings and text above refer to the implantation of a femoral component into a femoral bone for descriptive purposes only. Similar principles such as those described above could apply to other joints like the knee, ankle, feet, shoulder, elbow, back and wrist, with various modifications to account for anatomical and loading differences. For example, the sutures holes (190) in the vertical portions of the collar, shown in FIG. 8, could be applied to an implant for the shoulder joint to allow for a repair of the rotator cuff tendons (supraspinatus, subscapularis, and/or anterior capsule).

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

The invention claimed is:

1. A femoral prosthesis for implantation into a resected proximal end of a femur, the prosthesis comprising:
   a stem having a proximal end and a distal end,
   a collar portion for placement in a location adjacent the proximal end of the stem to engage at least a portion of the resected proximal end of the femur, wherein the collar portion comprises a substantially rigid material and includes an interior surface sized and configured to be at least partially in intimate contact with an unresected outer surface of the femur when the stem is implanted into the femur,
   wherein the interior surface includes a patient-specific portion at least partially in intimate contact with the unresected outer surface of the femur.

2. The femoral prosthesis of claim 1, wherein the collar portion is integrally attached to the stem.

3. The femoral prosthesis of claim 1, wherein the collar portion is modularly attached to the stem.

4. A femoral prosthesis for implantation into a resected proximal end of a femur, the prosthesis comprising:
   a stem having a proximal end and a distal end,
   a collar portion for placement in a location adjacent the proximal end of the stem to engage at least a portion of the resected proximal end of the femur, wherein the collar portion comprises a substantially rigid material and includes an interior surface sized and configured to be at least partially in intimate contact with an unresected outer surface of the femur when the stem is implanted into the femur,
   wherein at least a portion of the collar portion is pre-operatively shaped to substantially match one or more anatomical features of the patient.

5. The femoral prosthesis of claim 4, wherein the collar portion includes a non-circular opening for accommodating the stem.

6. The femoral prosthesis of claim 4, wherein the collar portion further comprises a horizontal lower surface substantially perpendicular to a longitudinal axis of the femur, the horizontal lower surface shaped to be in intimate contact with a first resected surface of the femur when the stem is implanted into the femur.

7. The femoral prosthesis of claim 6, wherein the collar portion further comprises a peripheral portion extending outward from the horizontal lower surface, the peripheral portion including a downwardly extending flanged portion having the inner surface sized and configured to be at least partially in intimate contact with the unresected outer surface of the femur when the stem is implanted into the femur.

8. The femoral prosthesis of claim 7, wherein the collar portion includes a central body, the central body having a top surface, a bottom surface and a body depth taken between the top and bottom surfaces along the longitudinal axis of the femur, the downwardly extending flange having a flange depth taken along the longitudinal axis of the femur that is less than the body depth.

9. The femoral prosthesis of claim 8, wherein at least one external surface of the central body includes a patient-specific portion that corresponds to an endosteal surface of the femur.

10. The femoral prosthesis of claim 8, wherein at least a portion of the inner surface of the downwardly extending flanged portion incorporates a patient-specific portion that corresponds to a periosteal surface of the femur.

11. The femoral prosthesis of claim 7, wherein the collar portion includes a central body, the central body having a top surface, a bottom surface and a body depth taken between the top and bottom surfaces along the longitudinal axis of the femur, the downwardly extending flange having a flange depth taken along the longitudinal axis of the femur that is greater than the body depth.

12. The femoral prosthesis of claim 7, wherein the flanged portion extends substantially parallel to the longitudinal axis of the femur.

13. The femoral prosthesis of claim 7, wherein the flanged portion extends substantially non-parallel to the longitudinal axis of the femur.

14. A femoral prosthesis for implantation into a resected proximal end of a femur, the prosthesis comprising a stem having a proximal end and a distal end a collar connected to the stem, the collar having a stem engagement portion for engaging the stem and a bone engagement portion for engaging a bone surface of the femur, wherein the collar includes an interior engagement surface having a patient-specific portion at least in intimate contact with an unresected periosteal surface of the femur, and the stem includes an exterior engagement surface configured to match at least a portion of an endosteal surface of the femur, wherein the collar further includes a resected bone engagement surface positioned between the interior engagement surface and the exterior engagement surface, the resected bone engagement surface configured to engage a resected bone surface of the femur.

15. The femoral prosthesis of claim 14, wherein the resected bone surface is a neck osteotomy of the femoral neck.

16. The femoral prosthesis of claim 15, wherein the collar substantially surrounds the entire periphery of the neck osteotomy.

17. The femoral prosthesis of claim 15, wherein the collar engages at least two opposing locations about a circumference of the neck osteotomy.

18. The femoral prosthesis of claim 14, wherein the stem engagement portion comprises a non-circular opening for accommodating the stem.

* * * * *